(12) United States Patent
Bickers et al.

(10) Patent No.: US 6,852,674 B2
(45) Date of Patent: Feb. 8, 2005

(54) HERBICIDAL MIXTURE COMPRISING A BENZOYL DERIVATIVE, A FERTILIZER CONTAINING NITROGEN AND AN ADJUVANT

(75) Inventors: Udo Bickers, Wietmarschen (DE); Erwin Hacker, Hochheim (DE); Frank Sixl, Selters-Haintchen (DE); Thomas Auler, Bad Soden (DE)

(73) Assignee: Aventis CropScience GmbH, Frankfurt (DE)

( * ) Notice: Subject to any disclaimer, the term of this patent is extended or adjusted under 35 U.S.C. 154(b) by 71 days.

(21) Appl. No.: 10/146,538

(22) Filed: May 14, 2002

(65) Prior Publication Data

US 2003/0104946 A1 Jun. 5, 2003

(30) Foreign Application Priority Data

May 16, 2001 (EP) ............................................. 01111821

(51) Int. Cl.⁷ ........................ A01N 41/10; A01N 43/09; A01N 43/16; A01N 43/80
(52) U.S. Cl. ....................... 504/271; 504/292; 504/294; 504/348
(58) Field of Search ................................ 504/271, 292, 504/294, 348

(56) References Cited

U.S. PATENT DOCUMENTS 5,658,855 A 8/1997 Nalewaja et al. ........... 504/214

FOREIGN PATENT DOCUMENTS

| WO | WO 92/19107 | 11/1992 |
| WO | WO 99/63823 | 12/1999 |
| WO | WO 00/21924 | 4/2000 |
| WO | WO 01/07422 A1 | 2/2001 |

*Primary Examiner*—S. Mark Clardy
(74) *Attorney, Agent, or Firm*—Frommer Lawrence & Haug LLP

(57) ABSTRACT

A method of controlling the growth of weeds at a locus which comprises applying to said locus a herbicidally effective amount of:

(a) a benzoyl derivative of formula (I):

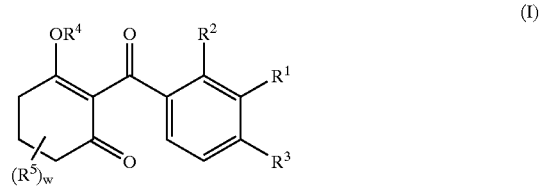

wherein $R^1$, $R^2$, $R^3$, $R^4$, $R^5$ and w are as defined in the description;

(b) a fertilizer containing nitrogen; and
(c) one or more adjuvants; and to their compositions thereof.

10 Claims, No Drawings

HERBICIDAL MIXTURE COMPRISING A BENZOYL DERIVATIVE, A FERTILIZER CONTAINING NITROGEN AND AN ADJUVANT

The invention relates to the technical field of herbicides, in particular to herbicidal compositions comprising certain benzoylcyclohexanediones in combination with nitrogen fertilizers and adjuvants, which are useful for the selective control of weeds and weed grasses in important plant crops. The invention also comprises a method of controlling undesirable vegetation in the presence of a crop, particularly a corn crop, by applying to the locus of the crop or undesired vegetation a herbicidal composition comprising a herbicidally effective amount of the benzoyl derivative, a fertilizer containing nitrogen and one or more adjuvants, optionally in mixture with additional herbicides or safeners.

There are many patent applications which describe benzoylcyclohexanedione herbicides. Certain benzoylcyclohexanedione compounds disclosed in WO 00/21924 and in WO 0107422 form a particularly useful class of such compounds. WO 9963823 discloses herbicidal mixtures containing a 3-heterocyclyl substituted benzoyl derivative of a pyrazole with an adjuvant and a fertilizer. WO 0053014 discloses herbicidal mixtures containing a 3-heterocyclyl substituted benzoyl derivative of a pyrazole with an adjuvant. WO 9219107 discloses herbicidal mixtures of certain 2-benzoyl-cyclohexane-1,3-dione derivatives with a nitrogen containing fertilizer and an adjuvant.

The use of the benzoylcyclohexanediones known from these patents is, however, frequently associated with disadvantages in practice. For example the herbicidal activity of the known compounds is not always adequate, or if the herbicidal activity is adequate undesired damage to the useful plants is observed.

Nitrogen is well known in the art as a fertilizer and is described in Farm Chemicals Handbook, 1988 Edition on pages B48 and B49. Commercially available nitrogen containing fertilizers include anhydrous ammonia, ammonium nitrate, ammonium sulfate, urea, nitrogen solutions (which include urea ammonium nitrate), potassium nitrate, and combinations thereof.

The term adjuvant includes surfactants, such as wetting agents, emulsifiers, dispersing agents and/or organic solvents, mineral and vegetable oils and combinations thereof. Adjuvants, especially those which are suitable for agrochemical use, are for example known from Foy, C. L., Adjuvants for agrichemicals, CRC Press Inc., Boca Raton, Fla., USA.

The applicants have found that the herbicidal performance of these compounds may be markedly improved using a combination of the benzoylcyclohexanedione compounds, together with a fertilizer containing nitrogen and one or more adjuvants.

The present invention provides a method of controlling the growth of weeds at a locus which comprises applying to said locus a herbicidally effective amount of:

(a) a benzoyl derivative of formula (I):

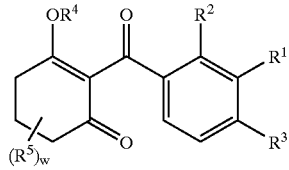

(I)

wherein:

$R^1$ is a formula (II):

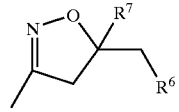

(II)

or $R^1$ is —$CH_2O$(haloalkyl), —$CH_2O$(alkyl), —$CH_2O$(cycloalkyl), —$CH_2OCH_2$(cycloalkyl), —$CH_2O(CH_2)_2O(CH_2)_2O$alkyl, —$CH_2S$(haloalkyl), —$CH_2OCH_2R^8$ or —$OCH_2$(cycloalkyl);

$R^2$ and $R^3$ independently of one another are hydrogen, halogen, cyano, nitro, —$S(O)_n$alkyl, —$S(O)_n$haloalkyl, alkyl, haloalkyl, alkoxy or haloalkoxy;

$R^4$ is hydrogen, —$SO_2$alkyl, —$CO$phenyl or —$SO_2$phenyl (the phenyl groups of which are optionally substituted by alkyl, haloalkyl, alkoxy, haloalkoxy, halogen, cyano or nitro);

$R^5$ is hydrogen or alkyl;

$R^6$ is cyano, $CONH_2$, $NHSO_2$alkyl, $NHSO_2$haloalkyl, $OR^9$, $CO_2$alkyl, —$S(O)_n$alkyl or —$S(O)_n$haloalkyl;

$R^7$ is hydrogen or alkyl;

$R^8$ is a 2-tetrahydrofuranyl, 3-tetrahydrofuranyl or 2-tetrahydropyranyl ring;

$R^9$ is hydrogen, alkyl, haloalkyl, alkenyl, haloalkenyl, alkynyl, cycloalkyl, cycloalkylalkyl or cycloalkenyl;

w is 1 or 2; and n is 0, 1 or 2;

or an agriculturally acceptable salt or metal complex thereof;

(b) a fertilizer containing nitrogen; and (c) one or more adjuvants.

Compounds of formula (I) in which $R^4$ is hydrogen may exist in a number keto or enolic tautomeric forms. Furthermore in certain cases the above substituents may contribute to optical isomerism and/or stereoisomerism. All such forms and mixtures are embraced by the present invention.

In the description unless otherwise specified the following terms are generally defined thus:

'alkyl' means a straight- or branched-chain alkyl group having one to six carbon atoms;
'haloalkyl' means a straight- or branched-chain alkyl group having one to six carbon atoms, substituted by one or more halogens;
'alkoxy' means a straight- or branched-chain alkoxy group having one to six carbon atoms;
'haloalkoxy' means a straight- or branched-chain alkoxy group having one to six carbon atoms, substituted by one or more halogens;
'alkenyl' means a straight- or branched-chain alkenyl group having two to six carbon atoms;
'haloalkenyl' means a straight- or branched-chain alkenyl group having two to six carbon atoms, substituted by one or more halogens;
'alkynyl' means a straight- or branched-chain alkynyl group having three to six carbon atoms;
'haloalkynyl' means a straight- or branched-chain alkynyl group having three to six carbon atoms, substituted by one or more halogens;
'cycloalkyl' means a three to six membered saturated carbocyclic ring;-

'cycloalkenyl' means a five or six membered mono unsaturated carbocyclic ring;

'halogen' means a fluorine, chlorine, bromine or iodine atom.

By the term "agriculturally acceptable salts" is meant salts the cations of which are known and accepted in the art for the formation of salts for agricultural or horticultural use. Preferably the salts are water-soluble. Suitable salts with bases include alkali metal (eg. sodium and potassium), alkaline earth metal (eg. calcium and magnesium), ammonium and amine (eg. diethanolamine, triethanolamine, octylamine, morpholine and dioctylmethylamine) salts.

By the term "metal complexes" is meant compounds wherein $R^4$ represents hydrogen (or a tautomer thereof) in which one or more of the oxygen atoms of the 2-benzoyl derivatives of formula (I) act as chelating agents to a metal cation. Examples of such cations include zinc, manganese, cupric, cuprous, ferric, ferrous, titanium and aluminium.

Fertilizers containing nitrogen are commonly classified as either nitrate or ammonium types. Commercially available ammonium types include anhydrous ammonia, aqueous ammonia, ammonium nitrate, ammonium sulfate, fluid nitrogen fertilizers and urea. The nitrate type fertilizers include ammonium nitrate, nitrogen solutions, calcium nitrate and sodium nitrate. The preferred fertilizers containing nitrogen are nitrogen solutions. The most preferred fertilizers containing nitrogen are urea ammonium nitrate (UAN) wherein the % N is from about 28% to about 33%; ammonium sulfate; urea; glycine, or mixtures thereof. The UAN solution and other nitrogen solutions can be prepared by processes known in the art.

The amount of fertilizer containing nitrogen used in the mixtures is generally from about 50–3000 g/ha, preferably from about 50–1500 g/ha, and more preferably from about 150–300 g/ha.

The present applicants have unexpectedly found that there is an optimal amount of fertilizer containing nitrogen present in the mixtures which provides the most effective weed control performance.

The preferred adjuvants are surfactants or organic liquids, the latter containing, if necessary, suitable emulsifiers to facilitate homogenous distribution of the liquid in the spray tank.

Surfactant types include nonionic, anionic, cationic and amphoteric surfactants. Examples of anionic surfactants include:
a) carboxylic acid salts, for example sodium and potassium salts of coconut oil fatty acids;
b) sulfonic acid salts, for example linear or branched chain alkyl benzene sulfonates, sodium, calcium and ammonium lignosulfonates, petroleum sulfonates, paraffin sulfonates and alkyl naphthalene sulfonates;
c) sulfuric acid ester salts, for example sulfated linear primary alcohols; and
d) phosphonic acid polyphosphonic acid esters, for example sodium alkyl phosphate; and
e) esters of phosphoric acid or sulfuric acid with ethoxylated di- and tristyrylphenols, as free acid or salt.

Examples of cationic surfactants include:
a) long chain amines;
b) quaternary ammonium salts, for example cetyltrimethyl ammonium bromide and N-alkyl trimethyl ammonium chloride; and
c) polyoxyethylenated long chain amines.

Examples of nonionic surfactants include:
a) polyoxyethylenated alkyl phenols;
b) polyoxyethylenated saturated and unsaturated fatty alcohols;
c) polyoxyethylenated polyoxypropylene glycols;
d) glyceryl and polyglyceryl esters of natural fatty acids;
e) ethoxylated sorbitan ester for instance Atplus 309 F;
f) alkanolamines;
g) tertiary acetylenic glycols;
h) polyoxyethylenated silicones;
i) N-alkyl pyrrolidones;
j) alkyl polyglycosides;
k) ethoxylated arylalkylphenols;
l) ethoxylated alkylphenols;
m) ethoxylated hydroxy-fatty acids, such as for example castor oil derivatives;
n) block-copolymers of ethyleneoxide and propyleneoxide; and
o) condensation products of EO-PO blockcopolymers and ethylendiamine.

Examples of amphoteric surfactants include:
a) beta-N-alkylaminopropionic acids;
b) N-alkyl-beta-iminodipropionic acids;
c) imidazoline carboxylates;
d) N-alkylbetaines;
e) amino oxides;
f) sulfobetaines or sultaines; and
g) phosphatides.

These surfactants and others are described in Drew Myers, Surfactants Science and Technology, (New York: VCH Publishers, Inc., 1988), Chapter 2 and Milton J. Rosen, Surfactants and Interfacial Phenomena, $2^{nd}$ Edition, (New York: John Wiley and Sons, Inc., 1989), Chapter 1.

Examples of organic liquids are:
1. Nonpolar solvents such as:
   a) aromatic hydrocarbons, i.e. derivatives of benzene, for example toluene, xylene, mesitylene, diisopropylbenzene, indane and derivatives of naphthalene such as 1-methylnaphthalene, 2-methylnaphthalene;
   b) aliphatic hydrocarbons, for example pentane, hexane, octane, cyclohexane and aliphatic and isoparaffinic mineral oils (Exol D, Isopor of EXXon);
   c) mixtures of aromatic and aliphatic hydrocarbons (Solvesso);
   d) halogenated aliphatic hydrocarbons such as methylene chloride; and
   e) halogenated aromatic hydrocarbons such as chlorobenzene or dichlorobenzene;
2. polar lipophilic liquids:
   a) vegetable or animal-oils fatty acid glycerol esters or fatty acid glycol esters, for example corn seed oil, cotton seed oil, linseed oil, soya oil, coconut oil, palm oil, thistle oil and castor oil;
   b) esters of saturated and unsaturated fatty acids (monocarboxylic acid monoesters), such as $(C_1-C_7)$ alkanecarboxylic acid-$(C_1-C_6)$alkylester, saturated and unsaturated $(C_8-C_{22})$ fatty acid-$(C_1-C_6)$ alkylesters such as alkyl esters of caprylic acid, capric acid, lauric acid, palmitic acid, stearic acid, oleic acid, linoleic acid, linolenic acid and derivatives of vegetable and animal oils such as alkylated rape seed oil;
   c) esters of aromatic carboxylic acids such as phthalic acid-$(C_1-C_{12})$ alkylester, especially phthalic acid-$(C_4-C_8)$alkylester;
   d) esters of other organic acids for example [$(C_1-C_{18}$alkyl]-phosphonic acid-di-[$(C_1-C_{12})$alkyl)- and/or -cycloalkyl]-ester, preferably a [(C$_4$–C$_{16}$alkyl]-phosphonic acid-di-(C$_1$–C$_{12}$)alkyl)-ester, in particular octanephosphonic acid-bis-(2-ethylhexyl)-ester (HOE S 4326, Clariant);

3. mixtures of solvents from classes 1) and/or 2) above.

Examples of preferred surfactants in the present invention include the following: polyoxyethylene sorbitan monolaurates; alkylaryl-polyoxyethylenes; paraffin based petroleum oil; polyoxyethylated polyol fatty acids and polyol fatty esters; crop oil concentrate; and silicone based additives.

In addition to the above surfactants, other inert adjuvants can also be incorporated into the compositions of this invention to provide a more satisfactory formulation. Such inert adjuvants include spreaders, emulsifiers, dispersing agents, foaming adjuvants, foam suppressants, penetrants and correctives.

The term herbicide is used herein to denote a compound which controls or modifies the growth of plants. The term plants is used to include all postemergent vegetation, ranging from seedlings to established vegetation.

The term fertilizer containing nitrogen is used herein to denote a primary nutrient that is required by all plants in considerable quantities for plant growth. The method of the present invention allows the grower to apply the fertilizer containing nitrogen, the adjuvant and the herbicide together in a single operation, which has the advantage of time and labour savings.

It has in addition unexpectedly been found that there is an optimal amount of surfactant present in the mixtures of the invention which provides the most effective weed control.

Preferred compounds of the invention are of formula (Ia):

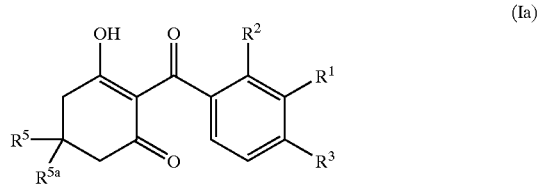

(Ia)

wherein:

R$^1$ is a formula (II):

(II)

or R$^1$ is —CH$_2$O-(halo-C$_1$–C$_4$-alkyl), —CH$_2$O—(C$_1$–C$_4$-alkyl), —CH$_2$O(CH$_2$)$_2$O(CH$_2$)$_2$O—C$_1$–C$_4$-alkyl, —CH$_2$OCH$_2$R$^8$ or —OCH$_2$—(C$_3$–C$_6$-cycloalkyl);

R$^2$ is methyl, —S(O)$_n$methyl, —S(O)$_n$ethyl or halogen;

R$^3$ is trifluoromethyl, —S(O)$_n$methyl, —S(O)$_n$ethyl or halogen;

R$^5$ and R$^{5a}$ are each hydrogen, methyl or ethyl;

R$^6$ is cyano or OR$^9$;

R$^7$ is hydrogen or C$_1$–C$_4$-alkyl;

R$^8$ is a 2-tetrahydrofuranyl or 3-tetrahydrofuranyl ring; and

R$^9$ is C$_1$–C$_4$-alkyl.

More preferred compounds of the invention are of formula (Ia) wherein:

R$^1$ is a formula (II):

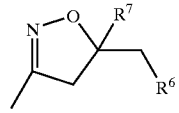

(II)

or R$^1$ is —CH$_2$O-(halo-C$_1$–C$_4$-alkyl) (wherein haloalkyl is preferably ethyl substituted by from one to five fluorine atoms), —CH$_2$O—(C$_1$–C$_4$-alkyl), —CH$_2$O(CH$_2$)$_2$O(CH$_2$)$_2$Omethyl, —CH$_2$OCH$_2$R$^8$ or —OCH$_2$(cyclopropyl);

R$^2$ is halogen or methyl;

R$^3$ is —S(O)$_n$methyl or —S(O)$_n$ethyl;

R$^5$ and R$^{5a}$ are each hydrogen or methyl;

R$^6$ is cyano or OR$^9$;

R$^7$ is hydrogen or methyl;

R$^8$ is a 2-tetrahydrofuranyl ring; and

R$^9$ is methyl or ethyl.

The most preferred compounds of formula (I) are:

2-[2-chloro-3-(5-cyanomethylisoxazolin-3-yl)-4-ethylsulfonylbenzoyl]cyclohexane-1,3-dione;
2-[2-chloro-3-(2,2,2-trifluoroethoxymethyl)-4-methylsulfonylbenzoyl]cyclohexane-1,3-dione;
2-{2-chloro-4-methylsulfonyl-3-[tetrahydrofuran-2-yl] methoxymethyl]benzoyl}cyclohexane-1,3-dione;
2-[2-chloro-3-(5-ethoxymethylisoxazolin-3-yl)-4-ethylsulfonylbenzoyl]cyclohexane-1,3-dione;
2-[2-chloro-3-(2,2-difluoroethoxymethyl)-4-ethylsulfonylbenzoyl]cyclohexane-1,3-dione;
2-[2-chloro-3-(methoxyethoxyethoxymethyl)-4-methylsulfonylbenzoyl]cyclohexane-1,3-dione;
2-[2-chloro-3-(5-methoxymethyl-5-methylisoxazolin-3-yl)-4-methylsulfonylbenzoyl]-cyclohexane-1,3-dione;
2-[2-chloro-4-ethylsulfonyl-3-(5-methoxymethyl-5-methylisoxazolin-3-yl)benzoyl]-cyclohexane-1,3-dione;
2-[2-chloro-3-(5-ethoxymethyl-5-methylisoxazolin-3-yl)-4-methylsulfonylbenzoyl]-cyclohexane-1,3-dione;
2-[2-chloro-4-ethylsulfonyl-3-(5-methoxymethyl-isoxazolin-3-yl)benzoyl]cyclohexane-1,3-dione;
2-[2-chloro-3-cyclopropylmethoxy-4-methylsulfonylbenzoyl]-5,5-dimethylcyclohexane-1,3-dione;
2-[2-chloro-3-cyclopropylmethoxy-4-methylsulfonylbenzoyl]cyclohexane-1,3-dione; and
2-[2-chloro-3-(1,1,2,2,2-pentafluoroethoxymethyl)-4-methylsulfonylbenzoyl]cyclohexane-1,3-dione.

The benzoyl derivatives of formula (I) may be prepared by known methods, for example as described in WO 00/21924 and WO 01/07422.

The mixtures according to the invention have an excellent herbicidal activity against a broad spectrum of economically important mono- and dicotyledonous harmful plants. The active substances also act efficiently on perennial weeds which produce shoots from rhizomes, root stocks or other perennial organs and are difficult to control.

Typical monocotyledonous and dicotyledonous weed flora which can be controlled by the compounds according to the invention include the following:

monocotyledonous weed species, for example, *Avena, Lolium, Alopecurus, Phalaris, Echinochloa, Digitaria,*

*Setaria* and *Cyperus* species from the annual group and, amongst the perennial species, *Agropyron, Cynodon, Imperata* and *Sorghum* and also perennial *Cyperus* species, and dicotyledonous weed species, for example, *Galium, Viola, Veronica, Lamium, Stellaria, Amaranthus, Sinapis, Ipomoea, Matricaria, Abutilon* and *Sida* amongst the annuals and *Convolvulus, Cirsium, Rumex* and *Artemisia* in the case of the perennial weeds.

Harmful plants occurring under the specific cultivation conditions of rice, such as, for example, *Echinochloa, Sagittaria, Alisma, Eleocharis, Scirpus* and *Cyperus*, are also outstandingly well controlled by the mixtures of the invention.

Although the mixtures according to the invention have an excellent herbicidal activity against mono- and dicotyledonous weeds, crop plants of economically important crops such as, for example, wheat, barley, rye, rice, maize, sugar beet, cotton and soybeans, are damaged only to an insignificant extent or not at all. For these reasons, the present mixtures are very suitable for the selective control of undesired vegetation in crops of agriculturally useful plants or in crops of ornamental plants.

On account of their herbicidal properties, the mixtures of the invention can also be employed for the control of harmful plants in crops of known genetically modified plants or genetically modified plants yet to be developed. As a rule, the transgenic plants are distinguished by particularly advantageous properties, for example by resistances to certain pesticides, especially certain herbicides, resistances to plant diseases or pathogens of plant diseases such as certain insects or microorganisms such as fungi, bacteria or viruses.

The mixtures according to the invention are preferably used in economically important transgenic crops of useful and ornamental plants, e.g. of cereals such as wheat, barley, rye, oats, millet, rice, cassava and corn or alternatively crops of sugar beet, cotton, soybeans, oilseed rape, potatoes, tomatoes, peas and other types of vegetables.

The mixtures of the invention can preferably be employed as herbicides in useful plant crops which are resistant or have been made genetically resistant to the phytotoxic effects of the herbicides.

The invention therefore also relates to the use of the above mixtures according to the invention as herbicides for controlling harmful plants in transgenic crop plants.

According to a further feature of the present invention, there are provided compositions which comprise:

(a) a herbicidally effective amount of a benzoyl derivative of formula (I) or an agriculturally acceptable salt or metal complex thereof;

(b) a fertilizer containing nitrogen; and (c) one or more adjuvants; in association with a herbicidally acceptable diluent or carrier and/or surface active agent.

The compounds of the formula (I) can be formulated in various ways, depending on what biological and/or chemicophysical parameters are prespecified. Examples of suitable formulation possibilities are: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), dispersions on an oil or water basis, oil-miscible solutions, capsule suspensions (CS), dusting agents (DP), dressing agents, granules for broadcasting and soil application, granules (GR) in the form of microgranules, spray granules, coated granules and adsorption granules, water-dispersible granules (WG), water-soluble granules (SG), ULV formulations, microcapsules and waxes.

These individual formulation types are known in principle and are described, for example, in: Winnacker-Küchler, "Chemische Technologie" [Chemical Technology], Volume 7, C. Hauser Verlag Munich, 4$^{th}$ Edition 1986, Wade van Valkenburg, "Pesticide Formulations", Marcel Dekker, N.Y., 1973; K. Martens, "Spray Drying" Handbook, 3rd Ed. 1979, G. Goodwin Ltd. London.

The necessary formulation auxiliaries such as inert materials, surfactants, solvents and other additives are also known and are described, for example, in: Watkins, "Handbook of Insecticide Dust Diluents and Carriers", 2nd Ed., Darland Books, Caldwell N.J., H.v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-Active Ethylene Oxide Adducts], Wiss. Verlagsgesell., Stuttgart 1976; Winnacker-Küchler, "Chemische Technologie" [Chemical Technology], Volume 7, C. Hauser Verlag Munich, 4$^{th}$ Edition 1986.

On the basis of these formulations, combinations with other pesticidally active substances such as, for example, insecticides, acaricides, herbicides, fungicides, and also with safeners, fertilizers and/or growth regulators can also be prepared, e.g. in the form of a finished formulation or as a tank mix.

Wettable powders are preparations which are uniformly dispersible in water and which, beside the active compound, also contain surfactants of ionic and/or nonionic type (wetting agents, dispersants), e.g. polyoxyethylated alkylphenols, polyoxethylated fatty alcohols, polyoxethylated fatty amines, fatty alcohol polyglycol ether sulfates, alkanesulfonates, alkylbenzenesulfonates, sodium lignosulfonates, sodium 2,2'-dinaphthylmethane-6,6'-disulfonates, sodium dibutylnaphthalene-sulfonates or alternatively sodium oleoylmethyltaurates in addition to a diluent or inert substance. For preparation of the wettable powders, the herbicidal active substances are finely ground, for example, in customary equipment such as hammer mills, blowing mills and air-jet mills and simultaneously or subsequently mixed with the formulation auxiliaries.

Emulsifiable concentrates are prepared by dissolving the active substance in an organic solvent, e.g. butanol, cyclohexanone, dimethylformamide, xylene or alternatively relatively high-boiling aromatics or hydrocarbons or mixtures of the organic solvents with addition of one or more surfactants of ionic and/or nonionic type (emulsifiers). Examples of emulsifiers which can be used are: alkylarylsulfonic acid calcium salts such as Ca dodecylbenzenesulfonate or nonionic emulsifiers such as fatty acid polyglycol esters, alkylaryl polyglycol ethers, fatty alcohol polyglycol ethers, propylene oxide-ethylene oxide condensation products, alkyl polyethers, sorbitan esters such as, for example, sorbitan fatty acid esters or polyoxyethylene sorbitan esters such as, for example, polyoxyethylene sorbitan fatty acid esters.

Dusting agents are obtained by grinding the active substance with finely divided solid substances, e.g. talc, natural clays, such as kaolin, bentonite and pyrophyllite, or diatomaceous earth.

Suspension concentrates can be water- or oil-based. They can be prepared, for example, by wet grinding by means of commercially available bead mills and, if appropriate, addition of surfactants, such as have already been mentioned, for example, above in the case of the other formulation types.

Emulsions, e.g. oil-in-water emulsions (EW), can be prepared, for example, by means of stirrers, colloid mills and/or static mixers using aqueous organic solvents and, if appropriate, surfactants, such as have already been mentioned.

Granules can either be prepared by spraying the active substance onto adsorptive, granulated inert material or by applying active substance concentrates to the surface of carriers such as sand, kaolinites or of granulated inert material by means of binders, e.g. polyvinyl alcohol, sodium polyacrylates or alternatively mineral oils.

Suitable active substances can also be granulated in the manner customary for the preparation of fertilizer granules—if desired as a mixture with fertilizers.

As a rule, water-dispersible granules are prepared by the customary processes such as spray-drying, fluidized bed granulation, disk granulation, mixing using high-speed mixers and extrusion without solid inert material.

For the preparation of disk, fluidized bed, extruder and spray granules, see, for example, processes in "Spray-Drying Handbook" 3rd ed. 1979, G. Goodwin Ltd., London; J. E. Browning, "Agglomeration", Chemical and Engineering 1967, pages 147 ff; "Perry's Chemical Engineer's Handbook", 5th Ed., McGraw-Hill, New York 1973, pp. 8–57.

For further details on the formulation of plant protection agents see, for example, G. C. Klingman, "Weed Control as a Science", John Wiley and Sons, Inc., New York, 1961, pages 81–96 and J. D. Freyer, S. A. Evans, "Weed Control Handbook", 5th Ed., Blackwell Scientific Publications, Oxford, 1968, pages 101–103.

As a rule, the agrochemical preparations contain 0.1 to 99% by weight, in particular 0.1 to 95% by weight, of active substance of the formula (I).

In wettable powders, the active substance concentration is, for example, approximately 10 to 90% by weight, the remainder to 100% by weight consists of customary formulation constituents. In the case of emulsifiable concentrates, the active substance concentration can be approximately 1 to 90, preferably 5 to 80, % by weight. Formulations in the form of dusts contain 1 to 30% by weight of active substance, preferably usually 5 to 20% by weight of active substance, sprayable solutions contain approximately 0.002 to 2%, preferably 0.01–0.2%, by weight of active substance. In the case of water-dispersible granules, the active substance content depends partly on whether the active compound is liquid or solid and which granulation auxiliaries, fillers etc. are used. In the case of water-dispersible granules, the content of active substance is, for example, between 1 and 95% by weight, preferably between 10 and 80% by weight.

In addition, the active substance formulations mentioned optionally contain the binders, wetting agents, dispersants, emulsifiers, penetrants, preservatives, antifreeze agents and solvents, fillers, carriers and colorants, antifoams, evaporation inhibitors and the pH and viscosity regulators which are customary in each case.

Components which can be employed for the active substances according to the invention in mixed formulations or in a tank mix are, for example, known active substances, such as are described, for example, in Weed Research 26, 441–445 (1986) or "The Pesticide Manual", 11th edition, The British Crop Protection Council and the Royal Soc. of Chemistry, 1997 and references cited there.

For use, the formulations present in commercially available form are diluted, if appropriate, in a customary manner, e.g. by means of water in the case of wettable powders, emulsifiable concentrates, dispersions and water-dispersible granules. Preparations in the form of dusts, soil or broadcasting granules and sprayable solutions are customarily not diluted further with other inert substances before use.

The application rate of the compounds of the formula (I) necessary varies with the external conditions such as, inter alia, temperature, humidity and the type of herbicide used. It can vary within wide limits, e.g. between 0.001 and 10.0 kg/ha or more of active substance, but is preferably between 0.005 and 5 kg/ha, and more preferably between 0.01 and 1 kg/ha.

According to a further feature of the present invention there is provided a product comprising:
(a) a herbicidally effective amount of a benzoyl derivative of formula (I) or an agriculturally acceptable salt or metal complex thereof;
(b) a fertilizer containing nitrogen; and
(c) one or more adjuvants; in association with a herbicidally acceptable diluent or carrier and/or surface active agent; as a combined preparation for separate, simultaneous or sequential use in the control of weeds at a locus.

It has unexpectedly been found that pre-mix formulations of the above ingredients (a), (b) and (c) provide an improved level of weed control and crop selectivity compared to tank mixtures, and accordingly the pre-mix formulations form a preferred aspect of the present invention.

The following non-limiting examples illustrate the method of the invention.

The compounds of formula (I) used in the Examples are given the following codes:

B1=2-[2-chloro-3-(2,2,2-trifluoroethoxymethyl)-4-methylsulfonylbenzoyl]cyclohexane-1,3-dione;
B2=2-[2-chloro-3-(5-cyanomethylisoxazolin-3-yl)-4-ethylsulfonylbenzoyl]cyclohexane-1,3-dione;
B3=2-{2-chloro-4-methylsulfonyl-3-[tetrahydrofuran-2-yl]methoxymethyl]benzoyl}cyclohexane-1,3-dione;
B4=2-[2-chloro-3-(methoxyethoxyethoxymethyl)-4-methylsulfonylbenzoyl]cyclohexane-1,3-dione; and
B5=2-[2-chloro-3-(1,1,2,2,2-pentafluoroethoxymethyl)-4-methylsulfonylbenzoyl]cyclohexane-1,3-dione.

The following codes are used for the various crop and weed species: HORVS=Barley; ORYSP=Transplanted Paddy Rice; ORYSW=Seeded Paddy Rice; ZEAMA=Maize; ABUTH=*Abutilon theophrasti*; AMARE=*Amaranthus retroflexus*; AVEFA=*Avena fatua*; CHEAL=*Chenopodium album*; CYPIR=*Cyperus iria*; CYPES=*Cyperus esculentus*; ECHCG=*Echinochloa crus-galli*; GALAP=*Galium aparine*; MATCH=*Matricaria chamomilla*; POLCO=*Polygonum convolvulus*; SETFA=*Setaria faberii*; SETLU=*Setaria lutescens*; SETVI=*Setaria viridis*; STEME=*Stellaria media*; and VIOTR=*Viola tricolor*.

In the following examples the herbicidal compounds characterized by "WP20" have been used as a wettable powder comprising 20% active ingredient, 20% Wessalon SV, 10% surfactant, 30% Texapon K12, 5% Calogon T, 0.2% Fluowet PP, 14.8% Kaolin W. The wettable powders have been made by processes known to one skilled in the art.

Other symbols used as abbreviations of formulation types are described at the end of table 12.

EXAMPLE 1

Weed Control Postemergence in the Greenhouse

Seeds of various crop and weed species were planted in a sandy-loamy soil and placed in a climate chamber in a greenhouse under good growth conditions. Four weeks after sowing, the plants were sprayed with a tank mixture containing the formulated test compound at a spray rate of 300 l/ha of spray solution. The plants were visually assessed fourteen days after application, and the percentage control of the plants is shown in Tables 1 and 2. The results show that the weed control for compounds B1 and B2 formulated with Hasten (soybean oil based adjuvant) is further improved by the addition of ammonium sulfate.

TABLE 1

| Mixture | Dose g a.i./ha | Percentage control | | | | |
|---|---|---|---|---|---|---|
| | | SETLU | ABUTH | MATCH | POLCO | VIOTR |
| B1 (WP20) | 75 | 58 | 85 | 43 | 43 | 65 |
| B1 (WP20) + Hasten | 75 1750 | 78 | 90 | 43 | 83 | 70 |
| B1 (WP20) + Hasten + Ammonium sulfate | 75 1750 3000 | 75 | 95 | 58 | 88 | 70 |

TABLE 2

| Mixture | Dose g a.i./ha | Percentage control | | | |
|---|---|---|---|---|---|
| | | ABUTH | AMARE | CHEAL | VIOTR |
| B2 (WP20) | 75 | 40 | 68 | 60 | 55 |
| B2 (WP20) + Hasten | 75 1750 | 75 | 83 | 95 | 65 |
| B2 (WP20) + Hasten + Ammonium sulfate | 75 1750 3000 | 90 | 85 | 98 | 70 |

EXAMPLE 2

Effect on Weeds in Rice

Seeds of the various weed species and rice crop varieties were planted in a sandy-loamy soil in a greenhouse under good growth conditions. Three weeks after sowing, the plants were sprayed with a tank mixture containing the formulated test compound at a spray rate of 600 l/ha of spray solution. The plants were visually assessed three weeks after application, and the percentage control of the plants is shown in Table 3. The results show that the weed control for compound B2 formulated with surfactants alone or with ammonium sulfate alone is dramatically improved by the addition of ammonium sulfate or a surfactant respectively whereas the damage in rice species is very low.

TABLE 3

| Mixture | Dose g a.i./ha | Percentage control | | | |
|---|---|---|---|---|---|
| | | Rice Variety | | Weed species | |
| | | Senia | Cypress | ECHCG | CYPES |
| B2 (WP20) | 50 | 0 | 0 | 0 | 15 |
| B2 (WP20) + Ammonium sulfate | 50 | 8 | 3 | 40 | 20 |
| B2 (WP20) + Hasten + Ammonium sulfate | 50 500 300 | 3 | 5 | 91 | 35 |

EXAMPLE 3

Effect on Weeds in Rice by Water Application

Seeds of the various weed species and rice were planted in a sandy-loamy soil in a greenhouse under good growth conditions. Three weeks after sowing the tank mixture containing the formulated test compound was applied to the plants submerged in the paddy water. The plants were visually assessed three weeks after application, and the percentage control of the plants is shown in Table 4 in comparison with untreated controls. The results show that the weed control for compound B2 formulated with ethylated soya oil is improved by the addition of ammonium sulfate. No rice damage was observed.

TABLE 4

| Mixture | Dose g ai/ha | Percentage control | |
|---|---|---|---|
| | | ORYSP | CYPES |
| B2 (WP20) | 12.5 | 0 | 45 |
| B2 (WP20) + Hasten | 12.5 500 | 0 | 40 |
| B2 (WP20) + Hasten + Ammonium sulfate | 12.5 500 300 | 0 | 75 |

EXAMPLE 4

Weed Control Postemergence in Maize Under Field Conditions

Using the method of Example 1 but in an outdoor pot trial in the field there were obtained the following results shown in Tables 5, 6 and 7. The results of Tables 5 and 6 show that the weed control for compound B2 formulated as a non aqueous suspension concentrate was improved by the addition of ammonium sulfate. No maize damage was observed. Table 7 illustrates the results using two different surfactants.

TABLE 5

| Mixture | g ai/ha | Percentage control | | | | | | | |
|---|---|---|---|---|---|---|---|---|---|
| | | ZEAMA | ECHCG | SETVI | SETLU | SETFA | ABUTH | CHEAL | GALAP |
| B2 (1K05 A1) | 50 | 0 | 48 | 68 | 70 | 75 | 30 | 78 | 25 |
| B2 (1K05 A1) + Ammonium sulfate | 50 100 | 0 | 83 | 85 | 75 | 85 | 48 | 83 | 45 |
| B2 (1K05 A1) + Ammonium sulfate | 50 300 | 0 | 78 | 73 | 80 | 93 | 55 | 95 | 60 |

TABLE 6

| Mixture | Dose g ai/ha | Percentage control | | | | | | | | |
|---|---|---|---|---|---|---|---|---|---|---|
| | | ZEAMA | AVEFA | ECHCG | SETVI | SETLU | SETFA | ABUTH | CHEAL | GALAP |
| B2 (1K05 A1) | 75 | 0 | 65 | 70 | 75 | 75 | 83 | 30 | 83 | 25 |
| B2 (1K05 A2) | 75 | 0 | 60 | 85 | 68 | 83 | 88 | 35 | 93 | 43 |
| B2 (1K05 A5) | 75 | 0 | 55 | 78 | 68 | 88 | 95 | 48 | 90 | 50 |

TABLE 7

| Mixture | Dose gai/ha | Percentage control | | | | | | | | |
|---|---|---|---|---|---|---|---|---|---|---|
| | | ZEAMA | AVEFA | ECHCG | SETVI | SETLU | SETFA | ABUTH | CHEAL | GALAP |
| B2 (1K03 A1) | 75 | 0 | 65 | 63 | 68 | 85 | 95 | 58 | 95 | 50 |
| B2 (1K03 A2) | 75 | 0 | 73 | 75 | 73 | 90 | 99 | 55 | 85 | 55 |

EXAMPLE 5

Weed Control Postemergence in the Greenhouse

Using the method of Example 1 the following results shown in Table 8 were obtained, which show that the weed control for compound B2 formulated as water based liquid formulations is improved by the addition of urea or glycine.

TABLE 8

| Mixture | Dose g a.i./ha | Percentage control | | | | |
|---|---|---|---|---|---|---|
| | | HORVS | ZEAMA | STEME | AMARE | CYPIR |
| B2 (00 SL05 A1) | 100 | 13 | 0 | 28 | 80 | 33 |
| B2 (00 SL05 A5) | 100 | 0 | 0 | 63 | 90 | 48 |
| B2 (00 SL05 A6) | 100 | 0 | 0 | 68 | 89 | 45 |

EXAMPLE 6

Weed Control Postemergence in an Outdoor Pot Trial

Using the method of Example 1 in an outdoor pot trial the following results shown in table 9 were obtained. The results show that the weed control for compound B2 formulated as oil dispersion 1K05 A1 is improved by the addition of ammonium sulfate, and in addition that there is an optimum amount of ammonium sulfate for efficacy enhancement. Ammonium sulfate in the range of 100 g/ha to 300 g/ha gave the best weed control.

TABLE 9

| Mixture | Dose g ai/ha | Percentage control | | | | | |
|---|---|---|---|---|---|---|---|
| | | ZEAMA | ECHCG | LOLMU | SETVI | ABUTH | GALAP |
| B2, 1K05A1 | 50 | 0 | 60 | 10 | 68 | 30 | 25 |
| B2, 1K05A1 + (NH$_4$)$_2$SO$_4$ | 50 100 | 0 | 48 | 13 | 85 | 48 | 45 |
| B2, 1K05A1 + (NH$_4$)$_2$SO$_4$ | 50 150 | 0 | 75 | 13 | 80 | 43 | 50 |
| B2, 1K05A1 + (NH$_4$)$_2$SO$_4$ | 50 300 | 0 | 83 | 18 | 73 | 55 | 63 |
| B2, 1K05A1 + (NH$_4$)$_2$SO$_4$ | 50 1000 | 0 | 78 | 15 | 73 | 50 | 60 |
| B2, 1K05A1 + (NH$_4$)$_2$SO$_4$ | 50 3000 | 0 | 60 | 13 | 68 | 45 | 45 |

EXAMPLE 7

Weed Control Postemergence in Greenhouse Trials

Using the method of Example 1 but with other compounds of formula (I), Table 10 shows that the weed control is improved by the addition of nitrogen fertilizer. The results also show the effects of varying the amount of nitrogen fertilizer, and that the weed control was greater using 300 g/ha compared with 300 g/ha of ammonium sulfate.

TABLE 10

| Mixture | Dose g ai/ha | Percentage control | | |
|---|---|---|---|---|
| | | SINAL | PHBPU | AVEFA |
| B4 (WP20) + 2 l ActirobB | 50 | 20 | 20 | 0 |
| B4 (WP20) + 2 l ActirobB + Ammonium sulfate | 50 300 | 65 | 70 | 20 |
| B4 (WP20) + 2 l ActirobB + Ammonium sulfate | 50 3000 | 60 | 55 | 0 |
| B5 (WP20) + 2 l ActirobB | 50 | 60 | 75 | 30 |
| B5 (WP20) + 2 l ActirobB + Ammonium sulfate | 50 300 | 70 | 80 | 35 |
| B5 (WP20) + 2 l ActirobB + Ammonium sulfate | 50 3000 | 60 | 45 | 30 |

EXAMPLE 8

Weed Control Postemergence in Greenhouse Trials

The method of Example 1 was repeated but employing varying amounts of surfactant. The results in Table 11 show that there is an optimum amount of surfactant for the best weed control. Thus 100 g/ha to 1000 g/ha of ActirobB, and 100 g/ha to 300 g/ha of GenapolX090 gave the best weed control, whilst higher amounts were less effective.

TABLE 11

| Mixture | Dose g ai/ha | Percentage control | | | |
|---|---|---|---|---|---|
| | | ALOMY | ECHCG | AMARE | CHEAL |
| B2 as WP20 | 100 | 30 | 40 | 35 | 58 |
| B2 as WP20 + ActirobB | 100 100 | 85 | 92 | 60 | 60 |
| B2 as WP20 + ActirobB | 100 1000 | 88 | 99 | 66 | 68 |
| B2 as WP20 + ActirobB | 100 2000 | 75 | 80 | 58 | 55 |
| B2 as WP20 + Genapol X090 | 100 100 | 90 | 88 | 60 | 70 |
| B2 as WP20 + Genapol X090 | 100 300 | 88 | 97 | 68 | 75 |
| B2 as WP20 + Genapol X090 | 100 1000 | 85 | 88 | 58 | 70 |

EXAMPLE 9

Weed Control Postemergence in an Outdoor Pot Trial

Using the method of Example 1 in an outdoor plot trial there were obtained the following results shown in Table 12. The results show that the weed control for compound B2 used as a pre-mix formulation as an oil dispersion 1K03 A1 is higher than that of the tank mixture of the wettable powder plus 2 l/ha of the surfactant ActirobB plus 3 kg/ha of ammonium sulphate.

TABLE 12

| Mixture | Dose g ai/ha | Percentage control | | |
|---|---|---|---|---|
| | | ZEAMA | SETVI | SETLU |
| B2 (WP20) | 50 | 0 | 48 | 35 |
| B2 (WP20) + ActirobB + Ammonium sulfate | 50 2000 3000 | 5 | 93 | 78 |
| B2 (1K03 A1) | 50 | 0 | 100 | 83 |

Surfactants Used in the above Tables:

Hasten=soybean oil based adjuvant
Atplus 309F=a nonionic surfactant containing coupling agents
Inex=adjuvant
Genapol X150=a nonionic surfactant based on ethoxylated isotridecanol polyglycol ether
Genapol X090=a nonionic surfactant based on ethoxylated isotridecanol polyglycol ether
Emulsogen EL400=a nonionic surfactant based on castor oil
ActirobB=rapeseed oil based adjuvant
RME=methylated rapeseed oil Formulations Used in the above Tables:

1K05 A1=a non-aqueous suspension concentrate containing a.i. (50 g/l), solvent (RME, 760 g/l) and Atplus 309F (120 g/l)

1K05 A2=a non-aqueous suspension concentrate containing a.i. (50 g/l), solvent (RME, 677 g/l), Atplus 309F (120 g/l) and ammonium sulfate (100 g/l)

1K05 A5=a non-aqueous suspension concentrate containing a.i. (50 g/l), solvent (RME, 625 g/l), Atplus 309F (120 g/l) and ammonium sulfate (150 g/l)

1K03 A1=a non-aqueous suspension concentrate containing a.i. (33 g/l), solvent (RME, 644 g/l), Atplus 309F (120 g/l) and ammonium sulfate (150 g/l)

1K03 A2=a non-aqueous suspension concentrate containing a.i. (33 g/l), solvent (RME, 647 g/l), Emulsogen EL400 (120 g/l) and ammonium sulfate (150 g/l).

SL05 A1=a water based liquid formulation containing a.i. (50 g/l) and Genapol X-150 (200 g/l)

SL05 A5=a water based liquid formulation containing a.i. (50 g/l), Genapol X-150 (200 g/l) and urea (5%)

SL05 A6=a water based liquid formulation containing a.i. (50 g/l), Genapol X-150 (200 g/l), urea (5%) and glycine (5%).

What is claimed is:

1. A method of controlling the growth of weeds at a locus which comprises applying to said locus a herbicidally effective amount of:

(a) a benzoyl derivative of formula (I):

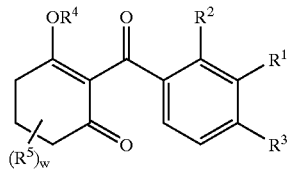

(I)

wherein:

$R^1$ is a formula (II):

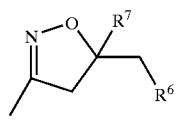

(II)

or $R^1$ is —CH$_2$O(haloalkyl), —CH$_2$O(alkyl)CH$_2$O (cycloalkyl), —CH$_2$OCH$_2$(cycloalkyl), —CH$_2$O (CH$_2$)$_2$O(CH$_2$)$_2$Oalkyl, —CH$_2$S(haloalkyl), —CH$_2$OCH$_2$R$^8$ or —OCH$_2$(cycloalkyl);

$R^2$ and $R^3$ independently of one another are hydrogen, halogen, cyano, nitro, —S(O)$_n$alkyl, —S(O)$_n$haloalkyl, alkyl, haloalkyl, alkoxy or haloalkoxy;

$R^4$ is hydrogen, —SO$_2$alkyl, —COphenyl or —SO$_2$phenyl (the phenyl groups of which are optionally substituted by alkyl, haloalkyl, alkoxy, haloalkoxy, halogen, cyano or nitro);

$R^5$ is hydrogen or alkyl;

$R^6$ is cyano, CONH$_2$, NHSO$_2$alkyl, NHSO$_2$haloalkyl, OR$^9$, CO$_2$alkyl, —S(O)$_n$alkyl or —S(O)$_n$haloalkyl;

$R^7$ is hydrogen or alkyl;

$R^8$ is a 2-tetrahydrofuranyl, 3-tetrahydrofuranyl or 2-tetrahydropyranyl ring;

$R^9$ is hydrogen, alkyl, haloalkyl, alkenyl, haloalkenyl, alkynyl, cycloalkyl, cycloalkylalkyl or cycloalkenyl;

w is 1 or 2; and n is 0, 1 or 2;

or an agriculturally acceptable salt or metal complex thereof;

(b) a fertilizer containing nitrogen; and (c) one or more adjuvants.

2. A method according to claim 1 in which the benzoyl derivative is of formula (Ia):

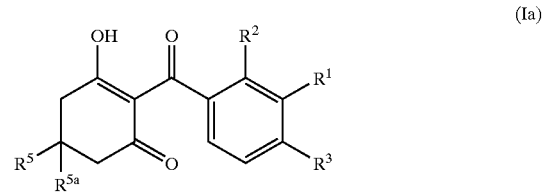

(Ia)

wherein:

$R^1$ is a formula (II):

(II)

or $R^1$ is —CH$_2$O-(halo-C$_1$–C$_4$-alkyl), —CH$_2$O—(C$_1$–C$_4$-alkyl), —CH$_2$O(CH$_2$)$_2$O—(CH$_2$)$_2$O C$_1$–C$_4$-alkyl, —CH$_2$OCH$_2$OCH$_2$R$^8$ or —OCH$_2$—(C$_3$–C$_6$-cycloalkyl);

$R^2$ is methyl, —S(O)$_n$methyl, —S(O)$_n$ethyl or halogen;

$R^3$ is trifluoromethyl, —S(O)$_n$methyl, —S(O)$_n$ethyl or halogen;

$R^5$ and $R^{5a}$ are each hydrogen, methyl or ethyl;

$R^6$ is cyano or OR$^9$;

$R^7$ is hydrogen or C$_1$–C$_4$-alkyl;

$R^8$ is a 2-tetrahydrofuranyl or 3-tetrahydrofuranyl ring; and $R^9$ is C$_1$–C$_4$-alkyl.

3. A method according to claim 1 in which the benzoyl derivative is of formula (Ia) wherein:

$R^1$ is a formula (II):

(II)

or $R^1$ is —CH$_2$O-(halo-C$_1$–C$_4$-alkyl), —CH$_2$O—(C$_1$–C$_4$-alkyl), —CH$_2$O(CH$_2$)$_2$O(CH$_2$)$_2$Omethyl, —CH$_2$OCH$_2$R$^8$ or —OCH$_2$(cyclopropyl);

$R^2$ is halogen or methyl;

$R^3$ is —S(O)$_n$methyl or —S(O)$_n$ethyl;

$R^5$ and $R^{5a}$ are each hydrogen or methyl;

$R^6$ is cyano or OR$^9$;

$R^7$ is hydrogen or methyl;

$R^8$ is a 2-tetrahydrofuranyl ring; and $R^9$ is methyl or ethyl.

4. A method according to claim 1 in which the benzoyl derivative is:

2-[2-chloro-3-(5-cyanomethylisoxazolin-3-yl)-4-ethylsulfonylbenzoyl]cyclohexane-1,3-dione;

2-[2-chloro-3-(2,2,2-trifluoroethoxymethyl)-4-methylsulfonylbenzoyl]cyclohexane-1,3-dione;

2-{2-chloro-4-methylsulfonyl-3-[tetrahydrofuran-2-yl]methoxymethyl]benzoyl}cyclohexane-1,3-dione;

2-[2-chloro-3-(5-ethoxymethylisoxazolin-3-yl)-4-ethylsulfonylbenzoyl]cyclohexane-1,3-dione;

2-[2-chloro-3-(2,2-difluoroethoxymethyl)-4-ethylsulfonylbenzoyl]cyclohexane-1,3-dione;

2-[2-chloro-3-(methoxyethoxyethoxymethyl)-4-methylsulfonylbenzoyl]cyclohexane-1,3-dione;

2-[2-chloro-3-(5-methoxymethyl-5-methylisoxazolin-3-yl)-4-methylsulfonylbenzoyl]-cyclohexane-1,3-dione;

2-[2-chloro-4-ethylsulfonyl-3-(5-methoxymethyl-5-methylisoxazolin-3-yl)benzoyl]-cyclohexane-1,3-dione;

2-[2-chloro-3-(5-ethoxymethyl-5-methylisoxazolin-3-yl)-4-methylsulfonylbenzoyl]-cyclohexane-1,3-dione;

2-[2-chloro-4-ethylsulfonyl-3-(5-methoxymethyl-isoxazolin-3-yl)benzoyl]cyclohexane-1,3-dione;

2-[2-chloro-3-cyclopropylmethoxy-4-methylsulfonylbenzoyl]-5,5-dimethylcyclo-hexane-1,3-dione;

2-[2-chloro-3-cyclopropylmethoxy-4-methylsulfonylbenzoyl]cyclohexane-1,3-dione; and 2-[2-chloro-3-(1,1,2,2,2-pentafluoroethoxymethyl)-4-methylsulfonylbenzoyl]cyclo-hexane-1,3-dione.

5. A method according to claim 1 in which the adjuvant is a surfactant or organic liquid.

6. A method according to claim 5 in which the adjuvant is a surfactant selected from polyoxyethylene sobitan monolaurates; alkylaryl-polyoxyethylenes; paraffin based petroleum oil; polyoxyethylated polyol fatty acids and polyol fatty esters; crop oil concentrate; and silicone based additives.

7. A method according to claim 1 in which the fertilizer is a nitrogen solution.

8. A method according to claim 7 in which the fertilizer is urea ammonium nitrate (UAN) wherein the % N is from 28% to 33%; ammonium sulfate, urea or mixtures thereof.

9. A composition comprising:
(a) a herbicidally effective amount of a benzoyl derivative of formula (I) as defined in claim 1 or an agriculturally acceptable salt or metal complex thereof;
(b) a fertilizer containing nitrogen
(c) one or more adjuvants.

10. A product comprising:
(a) a herbicidally effective amount of a benzoyl derivative of formula (I) as defined in claim 1 or an agriculturally acceptable salt or metal complex thereof;
(b) a fertilizer containing nitrogen
(c) one or more adjuvants as a combined preparation for separate, simultaneous or sequential use in the control of weeds at a locus.

* * * * *